United States Patent

Mete et al.

[11] Patent Number: 5,674,520
[45] Date of Patent: Oct. 7, 1997

[54] COMPOSITION CONTAINING A NITROMETHYLENE COMPOUND FOR USE IN COMBATING MOLLUSCS

[75] Inventors: Antionio Mete, Sittingbourne; David Munro, Maidstone; John Stewart Badmin, Faversham; Bipin Patel, Sittingbourne; Jamie Brian Mankee, Sittingbourne; Sarah Anne Davies, Sittingbourne, all of England

[73] Assignee: Shell Research Limited, United Kingdom

[21] Appl. No.: 220,420

[22] Filed: Mar. 31, 1994

[30] Foreign Application Priority Data

Apr. 1, 1993 [EP] European Pat. Off. ............ 93302602

[51] Int. Cl.⁶ ............................................ A01N 25/08
[52] U.S. Cl. .................... 424/410; 424/405; 514/379; 514/378; 514/365
[58] Field of Search .................... 424/84, 405, 408, 424/410, 417–427; 426/1; 514/379, 365, 378

[56] References Cited

U.S. PATENT DOCUMENTS

| | | | |
|---|---|---|---|
| 3,864,491 | 2/1975 | Bailey | 424/274 |
| 3,932,458 | 1/1976 | Bailey | 260/326.62 |
| 3,985,539 | 10/1976 | Bailey | 71/66 |
| 4,238,484 | 12/1980 | Stein et al. | 424/202 |
| 4,742,060 | 5/1988 | Shiokawa et al. | 514/252 |
| 4,968,695 | 11/1990 | Wolf et al. | 514/63 |
| 5,001,138 | 3/1991 | Shiokawa et al. | 514/342 |
| 5,162,308 | 11/1992 | Brown et al. | 514/63 |
| 5,204,332 | 4/1993 | Brown et al. | 514/63 |
| 5,204,360 | 4/1993 | Shiokawa et al. | 514/342 |
| 5,298,507 | 3/1994 | Skiokawa et al. | 514/256 |
| 5,360,906 | 11/1994 | Munro et al. | 544/331 |

FOREIGN PATENT DOCUMENTS

| | | |
|---|---|---|
| 192060 | 8/1986 | European Pat. Off. |
| 292822 | 11/1988 | European Pat. Off. |
| 302389 | 2/1989 | European Pat. Off. |
| 392560 | 10/1990 | European Pat. Off. |
| 437784 A1 | 7/1991 | European Pat. Off. |
| 555931 | 8/1993 | European Pat. Off. |

*Primary Examiner*—Neil S. Levy
*Attorney, Agent, or Firm*—Joseph M. Mazzarese

[57] ABSTRACT

1. The use of a compound of the general formula

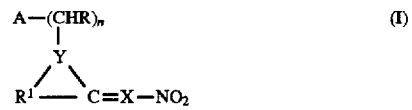

in which n is 0 or 1

Y represents a nitrogen atom or a CH group

X represents a nitrogen atom or a group $CR^2$ wherein $R^2$ represents a hydrogen atom, a nitro group or a substituted thio-methyl group A represents an optionally substituted 5- or 6- membered heterocyclic ring having one or two hetero atoms selected from nitrogen and oxygen, or an optionally substituted aryl, alkenyl or alkynyl group R, if present, represents a hydrogen atom or an alkyl group and $R^1$ represents a 3- or 4- membered alkylene chain optionally interrupted by a nitrogen and/or a sulphur atom, or having a terminal nitrogen and/or sulphur atom, for combating molluscs.

14 Claims, No Drawings

COMPOSITION CONTAINING A NITROMETHYLENE COMPOUND FOR USE IN COMBATING MOLLUSCS

The present invention relates to molluscicides and in particular to the molluscicidal use of certain nitromethylene compounds.

Nitromethylene compounds are well known for their insecticidal properties and have been the subject of many and varied patent disclosures.

It has now been found that certain substituted nitromethylene forms have a significant molluscicidal activity, particularly against gastropods, e.g. slugs and snails, and especially against slugs.

It has previously been suggested in European Patent Specification No. 437,784, that certain substituted nitromethylene imidazolidine derviatives are effective against soil pests such as slugs and snails; however, there are no test examples showing such molluscicidal activity. Tests using the slug, *Deroceras reticulatum*, now carried out on the compounds of Examples 2 and 3 of EP-A-437,784 detected no useful molluscicidal activity.

It is well known that many types of mollusc are agricultural and horticultural pests. Recent changes in farming practice have led to an increase in varieties of crops which are slug-susceptible, and the environmental pressures which prevent or restrict stubble-burning and encourage straw incorporation can be expected to aggravate existing mollusc, e.g. slug problems.

Current commercial sluggicides include metaldehyde and carbamates such as methiocarb. Carbamate molluscicides are highly effective but suffer from a high toxicity to mammals and other non-target organisms such as earthworms and hedgehogs. The metaldehyde molluscicide has a lower toxicity level but is not truly lethal to molluscs inducing a narcotic or dessicant effect to immobilise the mollusc pests.

There is a need for a useful molluscicide which is fully effective against, e.g. slugs and snails, but also has a low toxicity to non-target species, e.g. mammals.

The present invention provides the use of a compound of the general formula

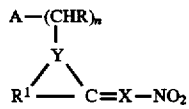  (I)

in which n is 0 or 1

Y represents a nitrogen atom or a CH group

X represents a nitrogen atom or a group $CR^2$ wherein $R^2$ represents a hydrogen atom, a nitro group or a substituted thiomethyl group A represents an optionally substituted 5- or 6- membered heterocyclic ring having one or two hetero atoms selected from nitrogen and oxygen, or an optionally substituted aryl, alkenyl or alkynyl group R, if present, represents a hydrogen atom or an alkyl group and and $R^1$ represents a 3- or 4- membered alkylene chain optionally interrupted by a nitrogen and/or a sulphur atom, or having a terminal nitrogen and/or sulphur atom, for combating molluscs.

An alkyl group may be a straight chain or branched chain group suitably containing up to 12 carbon atoms, preferably up to 6 and especially up to 4 carbon atoms. A preferred alkyl group is methyl. An alkenyl or alkynyl group suitably has from 2 to 12 carbon atoms, preferably from 2 to 6, and especially from 2 to 4, carbon atoms.

An aryl group may be a single or fused carbocyclic ring system having from 6 to 10 ring atoms, and is preferably a phenyl group or a naphthyl group.

A heterocyclic ring may be saturated or unsaturated. Preferred examples are pyridyl and isoxazolyl groups, but furanyl, pyranyl, pyrrolyl, imidazolyl, pyrazinyl, pyrimidinyl and pyridazinyl may also be mentioned.

Where substitutents are present, the substituent groups may be any of those customarily employed in the modification and/or development of pesticidal compounds and are especially substituents that maintain or enhance the molluscicidal activity associated with the compounds of the present invention, or influence persistence of action, or any other desirable property for molluscicidal compounds. There may be one or more of the same or different substituents present.

Suitable examples of optional substituents include halogen atoms, nitro groups, alkyl groups and haloalkyl groups halogen atoms may be fluorine, chlorine, bromine or iodine atoms. An alkyl moiety as an optional substituent or in such a substituent suitably has up to 6 carbon atoms, preferably up to 4, and especially 1 or 2 carbon atoms.

Preferred optional substituents are fluorine, chlorine or bromine atoms, nitro groups, methyl groups and trifluoromethyl groups.

Preferred compounds of formula I are those in which n is 0 or 1

Y represents a nitrogen atom

X represents a nitrogen atom or a group $CR^2$ in which $R^2$ represents a hydrogen atom, a nitro group or a group —$CH_2SR^3$ in which $R^3$ represents an unsubstituted or halo-substituted phenyl group A represents an isoxazole group, a pyridyl group or a phenyl group optionally substituted by one or more substituents independently selected from halogen atoms, $C_{1-4}$ alkyl groups and $C_{1-4}$ haloalkyl groups, or A represents a $C_{2-6}$ alkenyl group R, if present, represents a hydrogen atom and $R^1$ represents a group —$(CH_2)_m$Het— in which m is 2 or 3 and Het represents a sulphur atom or an NH group.

More preferred are the compounds of formula I in which n is 1, Y is N, X is N or CH, A is an isoxazole group substituted by chlorine, bromine, methyl, or trifluoromethyl, especially an isoxazole substituted by a chlorine atom or a methyl group, R is hydrogen, and $R^1$ is the group —$CH_2CH_2NH$—.

The present invention also encompasses a method of combating molluscs at a locus which comprises applying to the locus a compound of the general formula I given above, or a composition which comprises a compound of formula I and a carrier.

The compounds of formula I are nitromethylene derivatives, many of which are well known as potent insecticides. It is well documented that nitromethylene insecticides are of low mammalian toxicity, and, with the significant slug-toxicity activity now discovered, they offer an alternative to the carbamate/metaldehyde slugicides which have, to date, dominated the agricultural market.

The compounds of formula I may be utilised in conventional fashion for molluscicidal use, formulated for example into pellets or granules, suitable for ingestion by the target molluscs, which can be spread or located at a site of mollusc infestation, or an area liable to become infested by molluscs. Because of the systemic action of nitromethylene insecticides it is also feasible to use a compound of formula I in combating molluscs by spraying crops or crop areas liable to or actually infested by molluscs, in a suitable quantity to convey the molluscicicdal action to molluscs feeding on crop material. In addition to systemic action, control of molluscs could be achieved by direct contact of the nitromethylene derivatives of formula I. Other modes of use include incorporation the compound of formula I into a seed dressing thereby protecting, particularly, emerging seedlings from mollusc attack.

It is especially preferred that the compounds of formula I are used to combat slug and/or snail pests.

The locus to which a compound of formula I is to be applied by the method of the present invention, may therefore be a mollusc habitat or any area subject to or liable to mollusc attack and, for example, may be a plant, seed or the soil in a crop area.

The molluscicidal compounds of formula will usually be employed in the form of a composition in which the compounds are formulated with a carrier. For conventional molluscicidal treatment a food bait is utilised which may serve as, or be, additional to, the carrier. Such compositions have not previously been disclosed or suggested. The present invention therefore further provides a composition for combating molluscs which comprises, as active ingredient, a compound of formula I, a food bait for the mollusc, and, optionally, an additional carrier.

The term 'carrier' as used herein means any material with which the active ingredient is formulated to facilitate application to the locus to be treated or to facilitate storage, transport or handling. A carrier may be a solid or a liquid, including a material which is normally gaseous but which has been compressed to form a liquid, and any of the carriers normally used in formulating pesticidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloro-ethane. Mixtures of different liquids are often suitable.

For systemic application the compositions may be formulated and transported in a concentrated form which is subsequently diluted by the user before application. The presence of small amounts of a carrier which is a surface-active agent facilitates this process of dilution. Thus at least one carrier in a composition according to the invention may be a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention include a food bait for the mollusc, which may also act as carrier for the toxicant. The mollusc food bait may be wheat, corn barley, maize, rice, bran, oatmeal, groundnut, or any other vegetable product used for animal feeding. One or more of the following substances may be used as a supplement to the mollusc food bait, making food bait more palatable to the mollusc:

a) a B vitamin, particularly, B1, B2, B6, nicotinic acid or nicotinamide.

b) vitamin E.

c) an animal or vegetable proteinaceous material, for example, albuminoids and their hydrolytic degradative products, particularly those obtained by enzymic hydrolysis, for example, with pepsin, such as metaproteins, proteoses, peptones, polypeptides, peptides, diketopiperazines and amino carboxylic acids.

d) one or more amino carboxylic acids or their salts or amides which may be synthetic products.

e) a nucleic acid or a hydrolytic degradation product thereof such as a nucleotide, a nucleoside, adenine, guanine, cytosine, uracil or thymine.

f) urea, carbamic acid.

g) an ammonium salt, for example, ammonium acetate.

h) an amino sugar, for example, glucosamine or galactosamine.

i) sodium, potassium, calcium or magnesium compounds or trace amounts of manganese, copper, iron, cobalt, zinc, aluminum, boron or molybdenum compounds, particularly chelates thereof such as Versenes (Trade Mark).

j) phosphoric acid or glyceryl or sugar phosphates.

k) water.

The compositions may be formulated in any of the ways used for formulating pesticides. Particularly suitable formulations are granules or pellets, e.g. comprising 0.5–25, preferably 0.5 to 10, especially 0.5 to 4% by weight toxicant and up to about 50% by weight bait attractant. The granules or pellets may be manufactured by any of the known techniques, for example by agglomeration, extrusion, compaction or stick-on techniques. Granules are usually prepared to have a size between 10 and 100 BS mesh. The formulations may also include 0.1–5% by weight preservative, 0.5–20% by weight binding agents and 10–70% by weight slow release modifiers.

The incorporation of a preservative into the compositions inhibits the occurrence of fungal and/or bacterial growth on or in the compositions, and thus largely overcomes any problems of deterioration in use or from storage for long periods. Any food preservatives known to the art as having fungistatic or fungicidal and/or bacterial or bacteriostatic action may be used, for example sodium benzoate, methyl p-hydroxybenzoate, cetyl trimethyl ammonium bromide, citric acid, tartaric acid, sorbic acid, a phenol, an alkyl phenol or a chlorinated phenol.

In order to facilitate the formulations of the composition it may be desirable to incorporate into it one or more suitable binding agents such as alginic acid, alginates, alginate esters, starches, dextrins, cellulose derivatives and glues.

One or more slow release modifiers may be utilised in order to obtain a controlled release of the toxicant. Suitable release modifiers include clays such as bentonite or kaolinite, silicon oxides, polymeric materials such as cellulose, cellulose ethers, particularly cellulose acetate, and resins, for example urea formaldehyde resins, soya flour, waxes, stearates and oils, for example castor oil.

A suitable dye, for example a blue dye, may also be incorporated into the bait granules or pellets to render them unattractive to other forms of wild life, such as birds, and domestic animals.

The composition of the invention may also contain other active ingredients, for example plant protection agents such as compounds possessing herbicidal, insecticidal and fungicidal properties.

The compounds of general formula I are either nitromethylene pesticides known from literature or can be prepared in analogous manner to the procedures described for such compounds.

Reference should be made inter alia to European Patent Specifications Nos. 192,060; 292,822; 302,389; and 392,560.

In relation to the compounds of formula I in which A represents a 3-halo, especially a 3-chloro-substituted isoxazole, reference should be made to Applicants co-pending European Patent Application No. 93 200 385.8 (case reference T 1643) which describes a viable preparation route for such compounds.

The following Examples illustrate the invention.

EXAMPLE 1

The molluscicidal activity of compounds used in the method of the invention was tested using, as a test mollusc, specimens of the adult grey field slug *Deroceras reticulatum*.

The oral toxicity of the compounds was assessed by presenting slugs with individually prepared experimental baits containing either 4% or 2% active material. These were compared with commercial baits containing 4% methiocarb (Draza) in 6% metaldehyde (Slugit).

2 test pellets were placed onto a 5 cm filter-paper in the centre of a 9 cm plastic petri-dish. Two adults specimens of the slug *Deroceras reticulatum* were introduced into each dish and the pellets moistened with a few drops of water to make them attractive to eat. A minimum of the two replicates was used for each compound. Blank baits moistened with an equivalent volume of water were used as controls.

The dishes were then stored in a large glass tank maintained at 12° to 16° C. and >95% relative humidity. Assessments of the number of slugs affected were made at intervals up to 3 days after treatment. Slugs were considered to be affected or controlled by the bait if they were incapable of normal body movements and could not right themselves within 2 minutes.

The results are given in Table 3, presented as percentage control; Table 2 provides the structure of the test compounds, which are of the general formula:

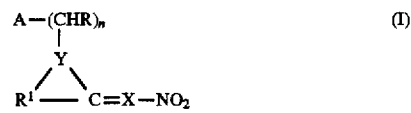

in which Y=N, R=2 H when n=1, and A, R¹, R², X and n are as given below:

TABLE 2

| Compound No. | A | R¹ | X | n |
|---|---|---|---|---|
| 1 | Cl, isoxazole | —CH₂CH₂NH— | CH | 1 |
| 2 | Cl, isoxazole | —CH₂CH₂NH— | N | 1 |
| 3 | CH₃, isoxazole | —CH₂CH₂NH— | CH | 1 |
| 4 | CF₃, isoxazole | —CH₂CH₂NH— | CH | 1 |

TABLE 2-continued

| Compound No. | A | R¹ | X | n |
|---|---|---|---|---|
| 5 | 3-Br-isoxazol-5-yl | —CH₂CH₂NH— | CH | 1 |
| 6 | 3-Br-isoxazol-5-yl | —CH₂CH₂NH— | N | 1 |
| 7 | 3-CH₃-isoxazol-5-yl | —CH₂CH₂S— | CH | 1 |
| 8 | 3-Cl-isoxazol-5-yl | —CH₂CH₂S— | CH | 1 |
| 9 | 3-Cl-isoxazol-5-yl | —CH₂CH₂NH— | C—NO₂ | 1 |
| 10 | 3-Br-isoxazol-5-yl | —CH₂CH₂NH— | C—CH₂—S—C₆H₄—Cl (4-Cl) | 1 |
| 11 | 3-CH₃-isoxazol-5-yl | —CH₂CH₂NH— | N | 1 |
| 12 | 6-Cl-pyridin-3-yl | —CH₂CH₂NH— | CH | 1 |
| 13 | 6-Cl-pyridin-3-yl | —CH₂CH₂NH— | N | 1 |
| 14 | 2,3-diCl-pyridin-5-yl | —CH₂CH₂NH— | CH | 1 |
| 15 | 2,3-diCl-pyridin-5-yl | —CH₂CH₂NH— | N | 1 |

TABLE 2-continued

| Compound No. | A | R¹ | X | n |
|---|---|---|---|---|
| 16 | 5,6-dichloropyridin-3-yl 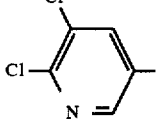 | —CH₂CH₂S— | CH | 1 |
| 17 | 6-chloropyridin-3-yl 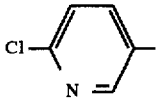 | —CH₂CH₂NH— | $\underset{C}{\text{CH}_2\text{SCH}_2\text{–Ph}}$ | 0 |
| 18 | 2,3,4-trifluorophenyl 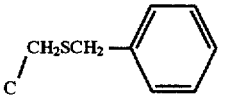 | —CH₂CH₂NH— | CH | 1 |
| 19 | 2-bromo-6-methylphenyl 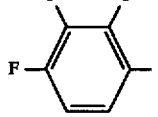 | —CH₂CH₂NH— | CH | 1 |
| 20 | naphthalen-1-yl 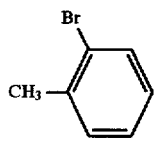 | —CH₂CH₂NH— | CH | 1 |
| 21 | 2-methyl-5-nitrophenyl 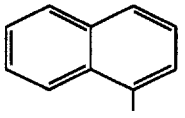 | —CH₂CH₂NH— | CH | 1 |
| 22 | 4-trifluoromethylphenyl 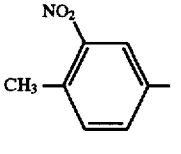 | —CH₂CH₂NH— | CH | 1 |
| 23 | isopropenyl 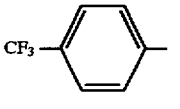 | —CH₂CH₂CH₂NH— | CH | 1 |
| 24 | 3-methylisoxazol-5-yl 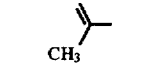 | —CH₂CH₂CH₂NH— | CH | 1 |

TABLE 3

| Compound No | % Active material in bait | % control |
|---|---|---|
| 1 | 4 | 100 |
| 2 | 2 | 50 |
| 3 | 2 | 100 |
| 4 | 2 | 100 |
| 5 | 2 | 50 |
| 6 | 2 | 25 |
| 7 | 2 | 100 |
| 8 | 2 | 25 |
| 9 | 2 | 50 |
| 10 | 2 | 25 |
| 11 | 2 | 100 |
| 12 | 4 | 20 |
| 13 | 4 | 30 |
| 14 | 4 | 20 |
| 15 | 2 | 25 |
| 16 | 2 | 50 |
| 17 | 2 | 25 |
| 18 | 2 | 25 |
| 19 | 2 | 25 |
| 20 | 2 | 25 |

TABLE 3-continued

| Compound No | % Active material in bait | % control |
|---|---|---|
| 21 | 2 | 25 |
| 22 | 2 | 50 |
| 23 | 2 | 25 |
| 24 | 2 | 25 |
| methiocarb | 4 | 100 |

It was observed that the Compounds acted to kill the slugs in the test, rather than merely controlled via a narcotic or desiccant action.

Bait palatability was monitored for Compounds Nos. 1, 3, 4 12, 13 and 14. On a scale which has a maximum palatability rating of +++, the compounds' palatability was assessed as follows:

| Compound No. | Bait Palatability |
|---|---|
| 1 | +++ |
| 3 | +++ |
| 4 | +++ |
| 12 | ++ |
| 13 | ++ |
| 14 | ++ |

COMPARISON EXAMPLE

The molluscicidal activity of two compounds specified in European Patent Specification No. 437 784 A1, was tested against slugs, *Deroceras reticulatum*, using the test method given in Example 1 and bait containing 4% active material in each case.

Comparative A is the compound of Example 2 of EP-A-437 784.

Comparative B is the compound of Example 3 of EP-A-437 784.

The results are given below

| | % Control | | | |
|---|---|---|---|---|
| | 3 hours | 1 day | 2 days | 3 days |
| A | 0 | 0 | 0 | 0 |
| B | 0 | 0 | 0* | 0 |

*In one replicate some activity against one slug was detected after 2 days but the effect was of transitory lethargy and the slug quickly recovered.

EXAMPLE 2

Systemic activity

The action via systemic application of the Compound Nos. 1, 3 and 4 was assessed in this Example.

Test solutions of the compounds were prepared by dissolving technical samples in 1 ml of acetone and making up to 50 ml with tap water. The roots of young 6 cm high lettuce plants were then washed clean with water and immersed in the test solution for a minimum of two days. For each bioassay individual leaves were cut from a lettuce plant and placed on a filter paper in a 9cm diameter petri-dish. 1 ml of water was pipetted onto each filter paper in order to keep the leaves reasonably moist during the assay. Two medium-sized slugs were introduced into each dish and the amount of leaf eaten and % control of slugs recorded over a two day period. The amount of compound applied as root dips was in the range of from 400 to 1000 ppm over a number of tests.

Slugs exposed to leaves of the treated plants showed signs of poisoning within three hours of exposure. Activity was observed at the 400 ppm (for Compounds nos. 1 and 3) and at the 1000 ppm for all of the test Compounds.

EXAMPLE 3

Contact Tests

The contact action of Compounds Nos. 1, 3 and 4 was assessed in this Example, using a glass residue test.

The residual toxicity of compounds on glass was investigated by pipetting aliquots of an acetone/Triton X-100 test solution over the base of a 7 cm diameter glass petri-dish to achieve a concentration of 600 ppm. Four adult slugs (*D. reticulatum*) were introduced into each dish and slug mortality recorded over a 5 day period. Moistened sugar bran mix was provided as food 24 hours after exposure.

The results are given below in Table 4.

TABLE 4

| Compound | | % affected *D. reticulatum* | | |
|---|---|---|---|---|
| No. | ppm | 24 hours | 48 hours | 120 hours |
| 1 | 600 | 100 | 75 | 100 |
| 3 | 600 | 75 | 100 | 100 |
| 4 | 600 | 25 | 0 | 25 |

EXAMPLE 4

The action of Compound No. 1 was assessed against a wide range of slug species, and against snails of the genus *Cepaea*, with bait containing 2%, 4% and 6% active ingredient. The action of a 4% Draza (trade name for a sluggicide sold by Bayer AG and containing the carbamate molluscicide methiocarb) bait was also assessed.

The slug species utilised in the test were

*Milax budapestensis*, a large slug which is a major pest of potatoes

*Deroceras reticulatum*, grey field slug—a major field crop pest

*Arion hortensis*, garden slug.

All slug species were controlled by the bait of the present invention with the 4% bait of the invention being more effective than the 4% Draza bait. *Cepaea* snails were also controlled with the bait of the invention.

We claim:

1. A composition for combating molluscs which comprises:

as active ingredient, a compound of the general formula

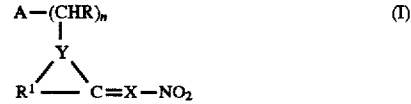

wherein n is 0 or 1,

Y represents a nitrogen atom,

X represents a nitrogen atom or a group $CR^2$ in which $R^2$ represents a hydrogen atom, a nitro group or a group —$CH_2SR^3$ in which $R^3$ represents an unsubstituted or halo-substituted phenyl group, A represents an isoxazole group, a pyridyl group, or a phenyl group optionally substituted by one or more substituents independently selected from the group consisting of halogen atoms, $C_{1-4}$ alkyl groups and $C_{1-4}$ haloalkyl groups, or A represents a $C_{2-6}$ alkenyl group, provided that A is not 6-chloro-3 pyridyl when: n is 1; X is $CR^2$; and $R^2$ is a group —$CH_2SR^3$ as defined above, R represents a hydrogen atom and $R^1$ represents a group —$(CH_2)_m$Het— in which m is 2 or 3 and Het represents a sulfur atom or an NH group;

a food bait for the molluscs;

and optionally, an additional carrier.

2. The composition of claim 1, wherein n is 1, Y is N, X is N or CH, A is an isoxazole group substituted by chlorine, bromine, methyl, or trifluoromethyl, R is hydrogen, and $R^1$ is the group —$CH_2CH_2NH$—.

3. The composition of claim 2, wherein A is an isoxazole group substituted by a chlorine atom or a methyl group.

4. A method of combating molluscs at a locus which comprises applying to the locus a compound of the formula I as specified in claim 1, or a composition which comprises such a compound together with a carrier.

5. A composition as claimed in claim 1, which contains in the range of from 0.5 to 10% by weight of compound of formula I.

6. A composition as claimed in claim 5, which contains in the range of from 0.5 to 4% by weight of compound of formula I.

7. A method of combating molluscs at a locus which comprises applying to the locus a molluscicidally effective amount of a compound of the formula

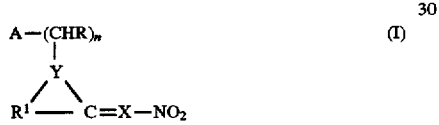

(I)

in which n is 0 or 1,

Y represents a nitrogen atom or a CH group,

X represents a nitrogen atom or a group $CR^2$ wherein $R^2$ represents a hydrogen atom, a nitro group or a substituted thiomethyl group in which the substituent is a phenyl or halo substituted phenyl group, A represents an optionally substituted 5- or 6-membered heterocyclic ring having one or two hetero atoms selected from the group consisting of nitrogen and oxygen, said optional substituents selected from the group consisting of halogen, nitro, and alkyl and haloalkyl groups having 1–12 carbon atoms, provided that A is not 6-chloro-3 pyridyl when: n is 1; R is hydrogen atom; X is $CR^2$; and $R^2$ is a substituted thiomethyl group as defined above, or an optionally substituted aryl group having 6–10 ring atoms and substituents selected from the group consisting of halogen atoms, 1–12 carbon alkyl groups and 1–12 carbon halo-alkyl groups, alkenyl group having 2–12 carbon atoms or alkynyl group having 2–12 carbon atoms, R if present represents a hydrogen atom or an alkyl group, and $R^1$ represents a 3- or 4-membered alkylene chain optionally interrupted by a nitrogen or a sulphur atom, or having a terminal nitrogen or sulphur atom.

8. The method as claimed in claim 7, wherein n is 0 or 1,

Y represents a nitrogen atom,

X represents a nitrogen atom or a group $CR^2$ in which $R^2$ represents a hydrogen atom, a nitro group or a group —$CH_2SR^3$ in which $R^3$ represents an unsubstituted or halo-substituted phenyl group, A represents an isoxazole group, a pyridyl group or a phenyl group optionally substituted by one or more substituents independently selected from the group consisting of halogen atoms, $C_{1-4}$ alkyl groups and $C_{1-4}$ haloalkyl groups, or A represents a $C_{2-6}$ alkenyl group, R, if present, represents a hydrogen atom, and $R^1$ represents a group —$(CH_2)_m$Het- in which m is 2 or 3 and Het represents a sulphur atom or an NH group.

9. The method of claim 8, wherein n is 1, Y is N, X is N or CH, A is an isoxazole group substituted by chlorine, bromine, methyl, or trifluoromethyl, R is hydrogen, and $R^1$ is the group —$CH_2CH_2NH$—.

10. The method of claim 9, wherein A is an isoxazole group substituted by a chlorine atom or a methyl group.

11. The method of claim 7, wherein said compound is applied as a composition comprising a carrier.

12. The method of claim 7, wherein said compound is applied together with a food bait for the mollusc.

13. The method of claim 11, wherein said compound is applied in an amount in the range of from 0.5 to 10% by weight based on the weight of the composition.

14. The method of claim 13, wherein said compound is applied in an amount in the range of from 0.5 to 4% by weight based on the weight of the composition.

* * * * *